US006630565B1

(12) United States Patent
Van Den Bergen et al.

(10) Patent No.: US 6,630,565 B1
(45) Date of Patent: Oct. 7, 2003

(54) PHOSPHORUS-COMPRISING MATERIALS, THEIR PREPARATION AND USE

(75) Inventors: Hugues Van Den Bergen, Brussels (BE); Jean-Claude Vanovervelt, Warchin (BE)

(73) Assignee: UCB, S.A., Brussels (BE)

( * ) Notice: Subject to any disclaimer, the term of this patent is extended or adjusted under 35 U.S.C. 154(b) by 0 days.

(21) Appl. No.: 09/913,794

(22) PCT Filed: Feb. 23, 2000

(86) PCT No.: PCT/EP00/01460
§ 371 (c)(1),
(2), (4) Date: Sep. 13, 2001

(87) PCT Pub. No.: WO00/52016
PCT Pub. Date: Sep. 8, 2000

(30) Foreign Application Priority Data

Feb. 26, 1999 (EP) .............................................. 99103736

(51) Int. Cl.[7] .............................................. C08G 79/02
(52) U.S. Cl. ..................... 528/400; 528/398; 528/403; 528/421; 528/487
(58) Field of Search ................................ 528/400, 398, 528/403, 421, 487

(56) References Cited

FOREIGN PATENT DOCUMENTS

| GB | 1 001 495 | 8/1965 |
|---|---|---|
| GB | 2 319 251 | 5/1998 |
| WO | 95/02004 | 1/1995 |

OTHER PUBLICATIONS

Kawakami et al; Long pot lifr epoxy resin coating copositions; Feb. 23, 1999; Chem Abstract 130:210864.*
Von Bonin et al; Resins prepared from polyepoxides, polyisocyanates, and acid esters of phosphorus containing acids; 1998; Chem Abstract 109:55917.*
Derouet et al., Journal of Applied Polymer Science, vol. 62, No. 11, pp. 1855–1868 (1996)—XP000635280.
Derouet et al., Rapra Abstracts, vol. 33, No. 12, p. 83 (1996)—XP000643586.

* cited by examiner

*Primary Examiner*—Duc Truong
(74) *Attorney, Agent, or Firm*—Wenderoth, Lind & Ponack, L.L.P.

(57) ABSTRACT

Phosphorus-comprising polyol, oligomer derived from this phosphorus-comprising polyol, polymer derived from this oligomer, processes for their preparation and uses of these. The present invention relates to a phosphorus-comprising polyol. The invention also relates to an oligomer derived from this phosphorus-comprising polyol and to the composition comprising this oligomer. The invention also relates to a polymer derived from this oligomer. The invention also relates to processes for the preparation of this phosphorus-comprising polyol, of this oligomer, of this polymer and of this composition. The invention also relates to the uses of this phosphorus-comprising polyol, of this oligomer, of this polymer and of this composition. The composition can be cross-linked by irradiation and exhibits flame-retardant properties.

14 Claims, No Drawings

PHOSPHORUS-COMPRISING MATERIALS, THEIR PREPARATION AND USE

The present invention relates to a phosphorus-comprising polyol. The invention also relates to an oligomer derived from this phosphorus-comprising polyol and to the composition comprising this phosphorus-comprising polyol and to the composition comprising this oligomer. The invention also relates to a polymer derived from this oligomer.

The invention also relates to processes for the preparation of this phosphorus-comprising polyol, of this oligomer, of this polymer and of this composition. The invention also relates to the uses of this phosphorus-comprising polyol, of this oligomer, of this polymer and of these compositions.

The composition which comprises the phosphorus-comprising polyol as constituent exhibits flame-retardant properties. The composition which comprises the oligomer can be cross-linked by irradiation and also exhibits flame-retardant properties.

The coatings industry is continually on the lookout for materials exhibiting an improved resistance to attacks and in particular an improved flame resistance.

Furthermore, this same industry is also on the lookout for materials which, while possessing the above improved resistance, are polymerisable in the form of a coating, as a thin or thick layer, while having recourse either to thermal curing or to one of the irradiation techniques, such as ultraviolet radiation or ionising radiation, such as gamma rays, X-rays or an electron beam.

Coatings having flame-retardant properties have already been obtained by polymerisation of compositions comprising phosphorus-comprising oligomers. Thus, U.S. Pat. No. 5,456,984 discloses a composition which can be polymerised by irradiation comprising an oligomer terminated by functional groups which can be copolymerised by irradiation, this oligomer being prepared from a polyisocyanate and a polyol comprising phosphorus in the phosphonate form, the oligomer reacting with a hydroxylated acrylate. The process for the preparation of the described composition is not easy, owing to the fact that the preparation of the polyol takes place in the presence of a solvent and a catalyst and that it is necessary to remove the water (abstract of Romanian Patent Application 88-134852 and abstract of Japanese Patent Application 81-48905) or the ethanol produced by azeotropic distillation and the solvent by vacuum distillation and the catalyst over a prolonged time.

Likewise, the preparation of another polyol (U.S. Pat. No. 5,456,984) comprising phosphorus in the phosphate and phosphonate form involves the use of alkylene oxides, the commonest of which are gases at atmospheric pressure, such as ethylene oxide, and therefore requires a specific industrial plant comprising appropriate reactors.

Furthermore, a phosphorus-comprising resin has already been described [D. Derouet, F. Morvan and J. C. Brosse, Journal of Applied Polymer Science, Vol. 62, 1855–1868 (1996)]; this resin has flame-retardant properties. The process for the preparation of this resin comprises the partial reaction between an epoxide compound, bisphenol A 4,4'-diglycidyl ether, and a dialkyl phosphate. The phosphorus-comprising epoxy resin which is thus prepared can be polymerised by heating in the presence of a cross-linking agent, such as a diamine (4,4'-diaminodiphenyl sulphone), and results in a composition having flame-retardant properties. However, this resin cannot be polymerised by irradiation and cannot therefore be applied to heat-sensitive substrates, such as fabrics, wood or paper. Furthermore, this polymerisation technique is expensive, on the one hand, in energy because of the heating and, on the other hand, in time, as the kinetics of polymerisation by heating are much slower than those by irradiation. Finally, a major disadvantage is the low content of phosphorus in the resin; the introduction of phosphorus into the epoxy resin takes place by opening the epoxide functional group and thus decreases the concentration of epoxide functional groups necessary for the polymerisation.

A demand therefore exists for a simple and economical process for the preparation of compounds of polyol type which comprise phosphorus atoms which can be used as starting material in the preparation of more complex compounds exhibiting flame-retardant properties.

To this end, the invention provides a process which does not require the presence of any solvent and of any catalyst. The separation of the final product from the solvent and catalyst is therefore unnecessary. It is not necessary to provide any separation and/or distillation stage. This simple process can therefore be employed at atmospheric pressure in a standard industrial plant. It is therefore particularly economical.

The invention provides a composition which has flame-retardant properties which are appreciably increased because of its phosphorus content. This composition can be cross-linked by irradiation and has flame-retardant properties. The composition of the invention can be applied to any type of substrate, such as, in particular, wood, textiles, paper and plastics, such as polyethylene and polypropylene.

The gases given off during the combustion of the composition according to the invention are less corrosive than those given off during the combustion of the known compositions which comprise halogens and consequently generate corrosive gases during the combustion. These corrosive gases, in addition to their toxic properties, cause significant damage to electronic components, present in particular in computers, which very often results in the loss of essential data and irreparable damage.

The invention provides a composition which makes it possible to obtain a coating which exhibits flame-retardant properties and good resistance to external conditions.

Furthermore, the invention provides a composition comprising one (or more) oligomer(s) having pendant phosphorus-comprising groups on the chain of this oligomer. This exhibits the advantage of avoiding cleavage of the chain during possible hydrolysis of this phosphorus-comprising group and of thus minimising the impact on the physicochemical and mechanical properties of the polymer obtained after cross-linking this composition by irradiation.

The present invention therefore overcomes the disadvantages of the known techniques.

To this end, the present invention provides a novel phosphorus-comprising polyol comprising at least two terminal phosphate ester groups or at least two terminal phosphonate ester groups or at least one terminal phosphate ester group and one terminal phosphonate ester group.

The term "polyol" is understood to mean a compound comprising at least two hydroxyl functional groups not bonded to the same carbon.

The term "terminal phosphate ester group" is understood to mean a group of general formula

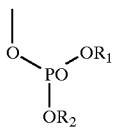

in which $R_1$ and $R_2$ independently represent a substituted or unsubstituted, aliphatic, cycloaliphatic or aromatic radical having from 1 to 16 carbon atoms.

The phosphate ester groups can be identical or different and they are preferably identical. The $R_1$ and $R_2$ radicals can be identical or different and they are preferably identical.

The term "terminal phosphonate ester group" is understood to mean a group of general formula

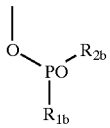

in which $R_{1b}$ represents a hydroxyl radical, a substituted or unsubstituted oxyalkyl or oxyaryl radical having from 1 to 16 carbon atoms, or a hydrogen atom; and $R_{2b}$ represents a substituted or unsubstituted, aliphatic, cycloaliphatic or aromatic radical having from 1 to 16 carbon atoms.

The phosphonate groups can be identical or different and they are preferably identical. The $R_{1b}$ and $R_{2b}$ radicals are preferably identical.

The phosphorus-comprising polyol of the invention usually comprises from 2 to 10 terminal phosphate or phosphonate groups. It preferably comprises 2 or 8 terminal phosphate or phosphonate groups. Good results have been obtained when it comprises 2 terminal phosphate or phosphonate groups.

The phosphorus-comprising polyol of the invention is usually the reaction product of at least one polyoxirane and of at least one phosphorus-comprising compound chosen from phosphoric acid esters, phosphonic acid esters, phosphonic acids, phosphinic acids and optionally phosphoric acid ($H_3PO_4$).

The term "phosphoric acid ester" is understood to mean a compound of general formula (I):

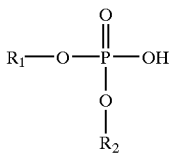

in which $R_1$ and $R_2$ independently represent a substituted or unsubstituted, aliphatic, cycloaliphatic or aromatic radical having from 1 to 16 carbon atoms.

Generally, in the formula (I), $R_1$ and $R_2$ independently represent a substituted or unsubstituted, aliphatic, cycloaliphatic or aromatic radical having from 1 to 12 carbon atoms.

Preferably, in the formula (I), $R_1$ and $R_2$ independently represent an aliphatic radical having from 1 to 10 carbon atoms or a phenyl radical which is substituted or unsubstituted.

Good results have been obtained when, in the formula (I), $R_1$ and $R_2$ independently represent a linear or branched, unsubstituted alkyl radical having from 1 to 8 carbon atoms, such as, in particular, the methyl, ethyl, propyl, isopropyl, primary normal butyl, secondary normal butyl, isobutyl or tertiary butyl radicals, or a phenyl radical.

Excellent results have been obtained when $R_1$ and $R_2$ represent a primary normal butyl radical.

The terms "phosphonic acid" and "phosphinic acid" are understood to mean a compound of general formula (II):

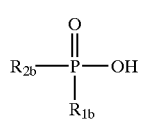

in which $R_{1b}$ represents a hydroxyl radical, a substituted or unsubstituted oxyalkyl or oxyaryl radical having from 1 to 16 carbon atoms, or a hydrogen atom; and $R_{2b}$ represents a substituted or unsubstituted, aliphatic, cycloaliphatic or aromatic radical having from 1 to 16 carbon atoms.

Generally, in the formula (II), $R_{1b}$ represents a hydroxyl radical or a hydrogen atom and $R_{2b}$ represents a substituted or unsubstituted, aliphatic, cycloaliphatic or aromatic radical having from 1 to 12 carbon atoms.

Useful results have been obtained when, in the formula (II), $R_{1b}$ represents a hydrogen atom (phosphinic acid) or a hydroxyl radical (phosphonic acid) and $R_{2b}$ represents a phenyl radical.

The term "polyoxirane" is understood to mean a compound comprising at least two oxirane radicals, that is to say at least two epoxide radicals, or at least two oxetanyl radicals, or at least one epoxide radical and at least one oxetanyl radical. The epoxide or oxetanyl radicals can be terminal or internal. They are preferably terminal. The polyoxirane comprising at least two epoxide radicals is named polyepoxide herein and the polyoxirane comprising at least two oxetanyl radicals is named polyoxetane herein.

The term "epoxide radical" is understood to mean a radical of general formula:

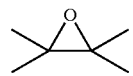

The term "oxetanyl radical" is understood to mean a radical of general formula:

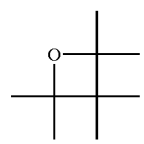

The polyoxirane is preferably a compound comprising at least two oxirane radicals. The polyoxirane preferably comprises from 2 to 5 oxirane radicals. Good results have been obtained when it comprises two or three oxirane radicals. Excellent results have been obtained when the polyoxirane comprises two epoxide radicals, that is to say is a diepoxide.

The polyepoxides of the invention are generally aliphatic, cycloaliphatic or aromatic polyepoxides. They are usually chosen from aliphatic, cycloaliphatic or aromatic glycidyl ethers or epoxy novolaks.

The aliphatic or cycloaliphatic polyepoxides can be saturated or unsaturated, linear or branched and substituted or unsubstituted. They can be monomeric or polymeric and liquid or solid but they are preferably liquid at room temperature.

Among aliphatic, cycloaliphatic or aromatic polyepoxides, glycidyl ethers which are well suited are those obtained by the reaction of epichlorohydrin with a dihydroxylated aliphatic, cycloaliphatic or aromatic compound. The term "aliphatic compound" is preferably understood to mean a compound comprising saturated or unsaturated, linear or branched alkylene groups. The term "cycloaliphatic compound" is preferably understood to mean an aliphatic compound comprising a cyclic part. The term "aromatic compound" is preferably understood to mean a compound comprising substituted or unsubstituted arylene groups. These definitions include the compounds comprising oxygen atoms.

Examples of polyepoxides which are well suited generally correspond to the general formula (III)

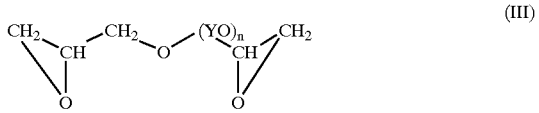

(III)

in which Y represents a divalent group chosen from aliphatic, cycloaliphatic, arylaliphatic or aryl groups comprising from 2 to 80 carbon atoms which can optionally comprise oxygen atoms and n represents an integer from 1 to 50. Y preferably represents an alkylene, cycloalkylene or arylene divalent group comprising from 2 to 60 carbon atoms and n represents an integer from 2 to 20.

Aliphatic glycidyl ethers which are particularly well suited are in particular polyalkylene glycol glycidyl ethers, such as polypropylene glycol and polyethylene glycol glycidyl ethers, and polytetrahydrofuran glycidyl ethers.

Good results have been obtained with the polypropylene glycol diepoxide sold by the company Dow under the name DER 732 and the polypropylene glycol diepoxide sold by the company Dow under the name DER 736.

Examples of polyepoxides which are also well suited correspond to the general formula (IV)

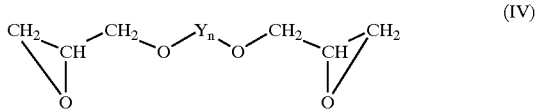

(IV)

in which Y represents a divalent group chosen from aliphatic, cycloaliphatic, arylatiphatic or aryl groups comprising from 2 to 80 carbon atoms and n represents an integer from 1 to 50. Y preferably represents a divalent alkylene, cycloalkylene or arylene group comprising from 2 to 60 carbon atoms and n represents an integer from 2 to 20.

Examples of aliphatic glycidyl ethers which are particularly well suited are in particular 1,4-butanediol, neopentyl glycol, cyclohexanedimethanol, 1,2-ethanediol or 1,6-hexanediol glycidyl ethers or trimethylolethane or trimethylolpropane triglycidyl ethers. Good results have been obtained with the 1,4-butanediol diglycidyl ether sold by the company Shell Chemical Company under the name Heloxy Modifier 67.

Other examples of aliphatic glycidyl ethers which are well suited are in particular polybutadiene oxide, epoxidised oils, such as the oil sold under the name Heloxy Modifier 505 ("Castor Oil") by the company Shell Chemical Company, glycerol oxypropylenated polyglycidyl ethers, such as the compound sold under the name Heloxy Modifier 84 by the company Shell Chemical Company, or carboxylic acid diglycidyl esters, such as the compound sold under the name Heloxy Modifier 71 by the company Shell Chemical Company and shown in the formula (V)

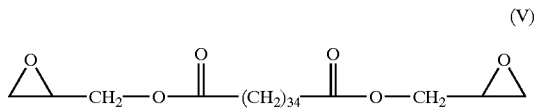

(V)

Examples of aromatic glycidyl ethers are those obtained from phenols or bisphenols comprising two hydroxyl groups, including in particular 2,2-bis(4-hydroxyphenyl) propane (bisphenol A), 2,2-bis(4hydroxy-3-tert-butylphenyl)propane, 1,1-bis(4-hydroxyphenyl)ethane, 1,1-bis(4-hydroxyphenyl)isobutane, bis(2-hydroxy-1-naphthyl) methane, 1,5-dihydroxynaphthalene, 1,1-bis(4-hydroxy-3-alkyl-phenyl)ethane, bisphenol F, 1,2-dihydroxybenzene, 1,3-dihydroxybenzene (1,3-resorcinol) or 1,4-dihydroxybenzene. Other examples of aromatic glycidyl ethers are o-di(2,3-epoxypropoxy)benzene (1,2-diglycidyloxybenzene), m-di(2,3-epoxypropoxy)benzene (1,3-diglycidykxybenzene) or p-di(2,3-epoxypropoxy) benzene (1,4-diglycidyloxy-benzene).

Examples of aromatic polyepoxides, commonly known as phenol/cresol novolaks, which are also well suited correspond to the general formula (VI):

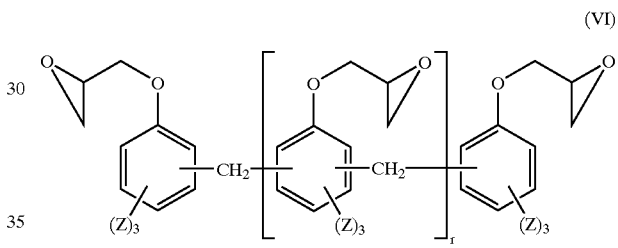

(VI)

in which Z independently represents a hydrogen atom or a linear or branched alkyl group comprising from 1 to 10 carbon atoms and r is an integer from 0 to 6.

Examples of cycloaliphatic glycidyl ethers which are particularly well suited are in particular the diglycidyl ethers of hydrogenated phenol comprising two hydroxyl groups, such as cyclohexanedimethanol diglycidyl ether.

Examples of polyepoxides which are also well suited correspond to the general formula (VII) or (VIII):

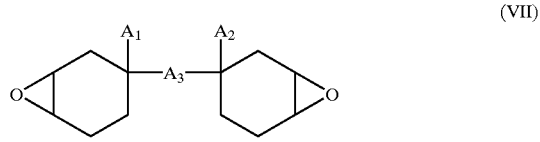

(VII)

(VIII)

in which $A_1$ and $A_2$ represent a hydrogen atom or form a ring which can optionally comprise one or more oxygen atoms and $A_3$ represents a divalent aliphatic group comprising from 1 to 20 carbon atoms which can optionally comprise ether or ester groups.

Examples of polyepoxides comprising two epoxide radicals (diepoxides) 15 which are well suited are in particular the 3,4-epoxycyclohexylmethyl ester of 3',4'-epoxycyclohexanecarboyxiuc acid, the 3,4-epoxytetrahydrobenzyl ester of 3',4'-epoxytetrahydrobenzoic acid or the 7'-oxabicyclo[4.1.0]-hept-3'-yimethyl ester of 7-oxabicyclo[4.1.0]heptane-3-carb-oxylic acid.

Other polyepoxides which are well known to a person skilled in the art can be chosen in particular from:
diepoxides of cycloaliphatic esters of dicarboxylic acids, such as those of formula (IX)

$$\text{(IX)}$$

in which m is an integer from 0 to 20 approximately, preferably from 1 to 6, and each of the carbon atoms of the aliphatic rings can carry one or two substituents, preferably hydrocarbonaceous substituents, which are preferably not very sterically hindered, such as linear alkyl radicals having from 1 to 9 carbon atoms approximately. Specific examples of such diepoxides of formula (IX) are bis(3,4-epoxycyclohexylmethyl) oxalate, bis(3,4-epoxycyclohexylmethyl) adipate and bis(3,4-epoxycyclohexylmethyl) pimelate.

3,4-epoxycyclohexylmethyl 3,4-epoxycyclohexanecarboxylates of formula (X)

$$\text{(X)}$$

in which each of the carbon atoms of the aliphatic rings can carry one or two substituents, preferably hydrocarbonaceous substitutents, which are preferably not very sterically hindered, such as linear alkyl radicals having from 1 to 9 carbon atoms. Specific examples of such diepoxides of formula (X) are 3,4-epoxycyclohexylmethyl 3',4'-epoxycyclohexanecarboxylate, 3,4-epoxy-1-methylcyclohexylmethyl 3',4'-epoxy-1'-methylcyclohexanecarboxylate, 6-methyl-3,4-epoxycyclohexylmethyl 6'-methyl-3',4'-epoxycyclohexanecarboxylate, 3,4-epoxy-3-methylcyclohexylmethyl 3,4'-epoxy-3'-methykyclohexanecarboxylate or 3,4-epoxy-5-methylcyclohexylmethyl 3',4'-epoxy-5'-methylcyclohexanecarboxylate. The diepoxide corresponding to the formula (X) without substituent is sold under the name Uvacure 1500 by the company UCB S.A. 3,4-epoxycyclohexanemethyl 3,4-epoxycyclohexanecarboxylates of formula (XI):

$$\text{(XI)}$$

in which n represents an integer from 1 to 30. Mention may be made, among these, of the compound sold under the name Celloxide 2081 (in which n is equal to 1), the compound sold under the name Celloxide 2083 (in which n is equal to 3) and the compound sold under the name Celloxide 2085 (in which n is equal to 5), which compounds are sold by the company Daicel.

Other polyepoxides can be chosen, such as, in particular, 1,2,5,6diepoxy-4,7-methanoperhydroindene, 2-(3,4-epoxycyclohexyl)-3',4'-epoxy-1,3-dioxane-5-spirocyclohexane, 1,2-ethylenedioxybis{3,4-epoxycyclohexylmethane), di(2,3-epoxycyclopentyl) Ether or diepoxycyclohexanes.

The compounds of formulae (IX) to (XI) and the compounds mentioned in the preceding paragraph can be prepared in particular according to the teaching of Crivello, J. V. and Lee, J. L., J. Polym. Sci., Poly. Chem 1990, Vol. 28, 479–503 and Crivello, J. V. Adv. in Polym. Sci., 1984, 62, 1.

Among the compounds of formulae (IX) to (XI), the best results were obtained with the diepoxides of formula (X) or of formula (XI) without substituents.

Examples of polyepoxides which are also well suited are the epoxy resins disclosed in International Patent Application WO 96/19516 and International Patent Application WO 96/19468 and also the polyepoxides disclosed in European Patent Application 0,139,042; the contents of these applications relating to epoxy resins are incorporated by reference.

Examples of polyoxetanes which are well suited correspond to the general formula (XII):

$$\text{(XII)}$$

in which Z represents a divalent oxyalkyl, oxycycloalkyl, oxyaryl or oxyalkyl-oxyaryl radical comprising from 1 to 50 carbon atoms, n represents an integer from 1 to 30 and $Z_1$ and $Z_2$ independently represent a monovalent aliphatic, cycloaliphatic or aromatic radical or an oxyalkyl, oxycycloalkyl, oxyaryl or oxyalkyl-oxyaryl radical comprising from 1 to 50 carbon atoms. Examples of polyoxetanes which are well suited are those disclosed in French Patent Application 2,758,557; the contents of this application are incorporated by reference.

Good results were obtained with one of these products, 1,4-bis[(3-ethyl-3-oxetanylmethoxy)methyl]-benzene, sold by the company Toagosei under the name XDO, which corresponds to the formula (XIII):

$$\text{(XIII)}$$

According to a preferred aspect, the phosphorus-comprising polyol of the invention corresponds to the general formula (XIV):

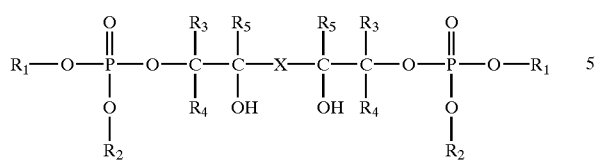

in which
- X represents a substituted or unsubstituted, divalent, linear or branched alkyl, cycloaliphatic or aromatic radical having from 1 to 50 carbon atoms which can optionally comprise oxygen atoms; or X represents a divalent group of general formula —X'—O—(X"—O)$_n$—X'"— in which n represents an integer from 1 to 50 and X', X" and X'" independently represent a substituted or unsubstituted, divalent, linear or branched alkyl, cycloaliphatic or aromatic radical having from 1 to 80 carbon atoms;
- $R_1$, $R_2$, $R_1'$ and $R_2'$ independently represent a substituted or unsubstituted, aliphatic, cyclo-aliphatic or aromatic radical having from 1 to 16 carbon atoms and/or optionally H;
- $R_3$, $R_4$, $R_3'$ and $R_4'$ independently represent a hydrogen atom or a substituted or unsubstituted, linear or branched alkyl, cycloaliphatic or aromatic radical having from 1 to 25 carbon atoms; and
- $R_5$ and $R_5'$ independently represent a hydrogen atom or a substituted or unsubstituted, linear or branched alkyl, cycloaliphatic or aromatic radical having from 1 to 25 carbon atoms.

Generally, in the formula (XIV),
- X represents a substituted or unsubstituted, divalent, linear or branched alkyl, cycloaliphatic or aromatic radical having from 1 to 50 carbon atoms which can optionally comprise oxygen atoms; or X represents a divalent group of general formula —X'—O—(X"—O)$_n$—X'"— in which n represents an integer from 1 to 20 and X', X" and X'" independently represent a substituted or unsubstituted, divalent, linear or branched alkyl, cycloaliphatic or aromatic radical having from 1 to 60 carbon atoms;
- $R_1$, $R_2$, $R_1'$ and $R_2'$ independently represent a substituted or unsubstituted, aliphatic, cycloaliphatic or aromatic radical having from 1 to 12 carbon atoms;
- $R_3$, $R_4$, $R_3'$ and $R_4'$ independently represent a hydrogen atom or a substituted or unsubstituted, linear or branched alkyl, cycloaliphatic or aromatic radical having from 1 to 20 carbon atoms; and
- $R_5$ and $R_5'$ independently represent a hydrogen atom or a substituted or unsubstituted, linear or branched alkyl, cycloaliphatic or aromatic radical having from 1 to 20 carbon atoms.

Preferably, in the formula (XIV),
- X represents a divalent group of general formula —X'—O—(X"—O)$_n$—X'"— in which n represents an integer from 1 to 8, and X' and X'" represent the CH$_2$ radical and X" represents a substituted or unsubstituted, divalent, linear or branched alkyl, cycloaliphatic or aromatic radical having from 1 to 12 carbon atoms;
- $R_1$, $R_2$, $R_1'$ and $R_2'$ independently represent a substituted or unsubstituted aliphatic radical having from 1 to 10 carbon atoms;
- $R_3$, $R_4$, $R_3'$ and $R_4'$ independently represent a hydrogen atom or an unsubstituted, linear or branched alkyl radical having from 1 to 15 carbon atoms; and
- $R_5$ and $R_5'$ independently represent a hydrogen atom or an unsubstituted, linear or branched alkyl radical having from 1 to 15 carbon atoms. Good results have been obtained when, in the formula (XIV), X represents a divalent group of general formula —X'—O—(X"—O)$_n$—X'"— in which n represents an integer from 1 to 7, X' and X'" represent the CH$_2$ radical and X" represents an unsubstituted, divalent, linear or branched alkyl or aryl radical having from 1 to 10 carbon atoms;
- $R_1$, $R_2$, $R_1'$ and $R_2'$ independently represent an unsubstituted, linear or branched alkyl radical having from 1 to 8 carbon atoms, such as in particular the methyl, ethyl, propyl, isopropyl, primary normal butyl, secondary normal butyl, isobutyl or tertiary butyl radicals;
- $R_3$, $R_4$, $R_3'$ and $R_4'$ independently represent a hydrogen atom or an unsubstituted, linear or branched alkyl radical having from 1 to 5 carbon atoms; and
- $R_5$ and $R_5'$ independently represent a hydrogen atom or an unsubstituted, linear or branched alkyl radical having from 1 to 5 carbon atoms.

Excellent results have been obtained when, in the formula (XIV),
- X represents a divalent group of general formula —X'—O—(X"—O)$_n$—X'"— in which
  n represents an integer from 1 to 7,
  X' and X'" represent the CH$_2$ radical, and
  X" represents an unsubstituted, divalent, linear or branched alkyl radical having from 1 to 10 carbon atoms, such as in particular the methyl, ethyl, propyl, isopropyl, primary normal butyl, secondary normal butyl, isobutyl or tertiary butyl radicals, or an unsubstituted divalent phenyl radical;
- $R_1$, $R_2$, $R_1'$ and $R_2'$ independently represent a primary normal butyl radical;
- $R_3$, $R_4$, $R_3'$ and $R_4'$ represent a hydrogen atom, and
- $R_5$ and $R_5'$ represent a hydrogen atom.

According to another preferred aspect, the phosphorus-comprising polyol of the invention corresponds to the general formula (XV):

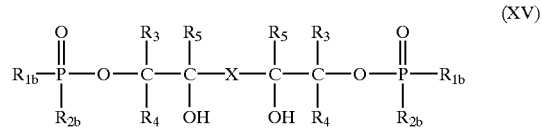

in which
- X represents a substituted or unsubstituted, divalent, linear or branched alkyl, cycloaliphatic or aromatic radical having from 1 to 50 carbon atoms which can optionally comprise oxygen atoms; or X represents a divalent group of general formula

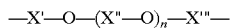

in which n represents an integer from 1 to 50 and X', X" and X'" independently represent a substituted or unsubstituted, divalent, linear or branched alkyl, cycloaliphatic or aromatic radical having from 1 to 80 carbon atoms;

$R_{1b}$ and $R_{1b}'$ represent a hydroxyl radical, a radical of substituted or unsubstituted oxyalkyl or oxyaryl type comprising from 1 to 16 carbon atoms or a hydrogen atom; and $R_{2b}$ and $R_{2b}'$ represent a substituted or unsubstituted, aliphatic, cycloaliphatic or aromatic radical having from 1 to 16 carbon atoms and/or optionally a hydroxyl radical;

$R_3$, $R_4$, $R_3'$ and $R_4'$ independently represent a hydrogen atom or a substituted or unsubstituted, linear or branched alkyl, cycloaliphatic or aromatic radical having from 1 to 25 carbon atoms; and $R_2$ and $R_5'$ independently represent a hydrogen atom or a substituted or unsubstituted, linear or branched alkyl, cycloaliphatic or aromatic radical having from 1 to 25 carbon atoms.

Generally, in the formula (XV),

X represents a substituted or unsubstituted, divalent, linear or branched alkyl, cycloaliphatic or aromatic radical having from 1 to 50 carbon atoms which can optionally comprise oxygen atoms; or X represents a divalent group of general formula

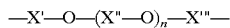

in which n represents an integer from 1 to 20 and X', X" and X'" independently represent a substituted or unsubstituted, divalent, linear or branched alkyl, cycloaliphatic or aromatic radical having from 1 to 60 carbon atoms;

$R_{1b}$ and $R_{1b}'$ represent a hydroxyl radical, a radical of substituted or unsubstituted oxyalkyl or oxyaryl type comprising from 1 to 16 carbon atoms or a hydrogen atom; and $R_{2b}$ and $R_{2b}'$ represent a substituted or unsubstituted, aliphatic, cycloaliphatic or aromatic radical having from 1 to 16 carbon atoms;

$R_3$, $R_4$, $R_3'$ and $R_4'$ independently represent a hydrogen atom or a substituted or unsubstituted, linear or branched alkyl, cycloaliphatic or aromatic radical having from 1 to 20 carbon atoms; and $R_5$ and $R_5'$ independently represent a hydrogen atom or a substituted or unsubstituted, linear or branched alkyl, cycloaliphatic or aromatic radical having from 1 to 20 carbon atoms.

Preferably, in the formula (XV)

X represents a divalent group of general formula

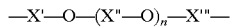

in which n represents an integer from 1 to 8, and X' and X'" represent the $CH_2$ radical and X" represents a substituted or unsubstituted, divalent, linear or branched alkyl, cycloaliphatic or aromatic radical having from 1 to 12 carbon atoms;

$R_{1b}$ and $R_{1b}'$ represent a hydroxyl radical, a radical of substituted or unsubstituted oxyalkyl or oxyaryl type comprising from 1 to 16 carbon atoms or a hydrogen atom; and $R_{2b}$ and $R_{2b}'$ represent a substituted or unsubstituted, aliphatic, cycloaliphatic or aromatic radical having from 1 to 16 carbon atoms;

$R_3$, $R_4$, $R_3'$ and $R_4'$ independently represent a hydrogen atom or an unsubstituted, linear or branched alkyl radical having from 1 to 15 carbon atoms; and $R_5$ and $R_5'$ independently represent a hydrogen atom or an unsubstituted, linear or branched alkyl radical having from 1 to 15 carbon atoms.

Good results have been obtained when, in the formula (XV),

X represents a divalent group of general formula

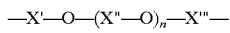

in which n represents an integer from 1 to 7, X' and X'" represent the $CH_2$ radical and X" represents an unsubstituted, divalent, linear or branched alkyl or aryl radical having from 1 to 10 carbon atoms;

$R_{1b}$ and $R_{1b}'$ represent a hydroxyl radical or a hydrogen atom, and $R_{2b}$ and $R_{2b}'$ represent a substituted or unsubstituted, aliphatic, cycloaliphatic or aromatic radical having from 1 to 10 carbon atoms;

$R_3$, $R_4$, $R_3'$ and $R_4'$ independently represent a hydrogen atom or an unsubstituted, linear or branched alkyl radical having from 1 to 5 carbon atoms; and $R_5$ and $R_5'$ independently represent a hydrogen atom or an unsubstituted, linear or branched alkyl radical having from 1 to 5 carbon atoms.

Excellent results have been obtained when, in the formula (XV)

X represents a divalent group of general formula

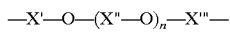

in which
n represents an integer from 1 to 7,
X' and X'" represent the $CH_2$ radical, and
X" represents an unsubstituted, divalent, linear or branched alky) radical having from 1 to 10 carbon atoms, such as in particular the methyl, ethyl, propyl, isopropyl, primary normal butyl, secondary normal butyl, isobutyl or tertiary butyl radicals, or an unsubstituted divalent phenyl radical;

$R_{1b}$ and $R_{1b}'$ represent a hydroxyl radical or a hydrogen atom, and $R_{2b}$ and $R_{2b}'$ represent a phenyl radical;

$R_3$, $R_4$, $R_3'$ and $R_4'$ represent a hydrogen atom and $R_5$ and $R_5'$ represent a hydrogen atom.

The present invention also relates to a process for the preparation of the phosphorus-comprising polyol.

A preparation process comprises the reaction of at least one polyoxirane and of at least one phosphorus-comprising compound chosen from phosphoric acid esters, phosphonic acid esters, phosphonic acids and phosphinic acids. Several polyoxiranes and/or several phosphorus-comprising compounds can be employed during the process. Preferably, one polyoxirane and one phosphorus-comprising compound are employed.

The polyoxiranes and the phosphorus-comprising compounds which can be employed in the process according to the invention have been defined above.

Excellent results have been obtained when the polyoxirane employed in the process of the invention is chosen from propylene glycol diepoxides, 1,4-butanediol glycidyl ether, the diepoxides of formula (X) or (XI) sold under the names Uvacure 1500 by the company UCB S.A. or Celloxide 2021P, Celloxide 2081, Celloxide 2083 or Celloxide 2085 by Daicel, 1,4-bis[(3-ethyl-3-oxetanylmethoxy) methyl]benzene, sold by Toagosei under the name XDO, the aromatic diepoxide (bisphenol A diglycidyl ether) sold under the name Epikote 828 by the company Dow Chemical, and the cycloaliphatic polyepoxides of general formula (VI), such as the cresol novolak sold by the company Dow Chemical under the name DEN 431.

Excellent results have been obtained when the phosphoric acid ester employed in the process of the invention is dibutyl phosphate.

Excellent results have been obtained when the phosphonic acid employed in the process of the invention is phenylphosphonic acid.

Excellent results have been obtained when the phosphinic acid employed in the process of the invention is phenylphosphinic acid.

The molar ratio of the phosphorus-comprising compound to the polyoxirane employed in the process of the invention mainly depends on the number of oxirane radicals which the polyoxirane comprises. At least one equivalent of oxirane radical carried by the polyoxirane is employed per mol of phosphorus-comprising compound. In general, less than 2 equivalents of oxirane radical are employed. Preferably, the equivalent number is between 1 and 1.5. In a particularly preferred way, it is in the region of 1.

The preparation of the phosphorus-comprising polyol according to the invention is normally carried out in the absence of solvent. However, it can be carried out in the presence of solvent, such as toluene and xylene. Nevertheless, as the solvent contributes no major advantage, it is preferably carried out in the absence of solvent.

The preparation of the phosphorus-comprising polyol according to the invention is normally carried out in the absence of catalyst. However, it can be carried out in the presence of catalysts, such as phosphoric acid or its corresponding aliphatic or aromatic esters, inorganic alkali metal salts (such as sodium carbonate), organometallic salts (such as lithium octanoate), ammonium salts, such as benzyltrimethylammonium chloride, tertiary amines (such as triethylamine, triethanolamine, dicycloctadiamine or N,N-dimethylaniline), potassium hydroxide, divalent metal oxides or hydroxides, or chromium catalysts, such as a catalyst sold by the company Aerojet Solid Propulsion Company under the name AMC-2. Nevertheless, as the catalyst contributes no major advantage, the preparation of the phosphorus-comprising polyol is preferably carried out in the absence of catalyst.

The reaction temperature for the preparation of the phosphorus-comprising polyol of the invention is generally between approximately 20° C. and 150° C. It is preferably between approximately 30 and 120° C. In a particularly preferred way, it is between approximately 50° C. and 100° C. Good results have been obtained with a reaction temperature of between approximately 60° C. and 95° C.

The reaction pressure for the preparation of the phosphorus-comprising polyol of the invention depends on the nature of the components employed and in particular on the physical state (gas, liquid or solid) of the polyoxirane at the reaction temperature. As the majority of polyoxiranes are liquid or solid at atmospheric pressure and room temperature, the pressure used is therefore generally identical to atmospheric pressure.

The degree of progression of the reaction can be monitored by any known means, such as, in particular, the measurement of the acid number or epoxy value of the reaction medium or the use of proton or phosphorus NMR.

The present invention also relates to the use of the phosphorus-comprising polyol.

The phosphorus-comprising polyol of the invention can be used in particular as additive in the preparation of flame-retardant compositions. It can be employed in particular in compositions which can be cross-linked by irradiation. The phosphorus-comprising polyol of the present invention can be used in the preparation of polyurethanes and particularly of polyurethane-(meth)acrylates which can be cross-linked by irradiation.

To this end, the present invention also relates to an oligomer which is the product of the reaction of a phosphorus-comprising polyol as defined above, of a polyisocyanate and of a hydroxylated acrylate.

The oligomer of the invention is composed of a phosphorus-comprising polyol and of a polyisocyanate terminated by at least one hydroxylated derivative comprising one or more unsaturations. The oligomer is therefore a urethane- acrylate compound.

The term "polyisocyanate" is understood to mean a compound comprising at least two isocyanate (NCO) functional groups per molecule.

An organic polyisocyanate, such as an aliphatic, cycloaliphatic or aromatic polyisocyanate, is generally employed. Mention may be made, as examples of appropriate aliphatic diisocyanates, of 1,4-diisocyanatobutane, 1,6-diisocyanatohexane, 1,6-diisocyanato-2,2,4-trimethylhexane and 1,12-diisocyanatodecane.

Appropriate cycloaliphatic diisocyanates comprise 1,3- and 1,4-diisocyanatocyclohexane, 2,4-diisocyanato-1-methylcyclohexane, 1,3-diisocyanato-2-methylcyclohexane, 1-isocyanato-2-(isocyanatomethyl) cyclopentane, 1,1'-methylenebis[4-isocyanatocyclohexane], 1,1'-(1-methyl ethylidene)bis[4-isocyanatocyclohexane], 5-isocyanato-1-isocyanatomethyl-1,3,3-trimethylcyclohexane (isophorone diisocyanate), 1,3- and 1,4-bis(isocyanatomethyl)cyclohexane, 1,1'-methylenebis [4-isocyanato-3-methylcyclohexane], 1-isocyanato-4(or 3)-isocyanatomethyl-1-methylcyclohexane and dicyclohexylmethane diisocyanate.

Aromatic diisocyanates which are particularly appropriate comprise toluene 2,4-diisocyanate, 1,4-diisocyanatobenzene, 1,1'-methylenebis[4-isocyanatobenzene], 2,4-diisocyanato-1-methylbenzene, 1,3-diisocyanato-2-methylbenzene, 1,5-diisocyanatonaphthalene, 1,1'-(1-methylethylidene)bis[4-isocyanatobenzene], 1,3- and 1,4-bis(1-isocyanato-1-methylethyl)benzene and diphenylmethane diisocyanate.

Aromatic or aliphatic polyisocyanates comprising 3 or more isocyanate groups can also be used, such as, for example, 1,1',1"-methylidynetris[4-isocyanatobenzene], the trimer of hexamethylene diisocyanate and the polyphenylpolymethylene polyisocyanates obtained by phosgenation of aniline/formaldehyde condensates.

Preferably, a diisocyanate is employed. In a particularly preferred way, toluene diisocyanate, isophorone diisocyanate, trimethylhexane diisocyanate, dicyclohexylmethane diisocyanate, diphenylmethane diisocyanate, hexamethylene diisocyanate, naphthalene diisocyanate, phenylene diisocyanate or diphenyl diisocyanate is employed. Good results have been obtained with isophorone diisocyanate (IPDI).

The term "hydroxylated acrylate" is understood to mean a compound comprising at least one acrylate or methacrylate functional group and at least one hydroxyl functional group. Generally, a monohydroxylated acrylate is employed. Hydroxymethyl acrylate, hydroxyethyl acrylate, hydroxypropyl acrylate or hydroxybutyl acrylate is usually employed. Other unsaturated monohydroxylated derivatives can also be used, such as methacrylate analogues, vinyl ethers, allyl ethers, vinyl esters, itaconates or crotonates. Preferably, hydroxyethyl acrylate is employed.

The reaction of a polyisocyanate with a polyol in order to produce an oligomer comprising urethane groups is well known to a person skilled in the art. It is therefore unnecessary to describe the reaction conditions.

According to another aspect, the present invention also relates to an oligomer produced by the reaction of a phosphorus-comprising polyol as defined above with the alkyl esters of acrylic acid or methacrylic acid.

This reaction can be carried out by transesterification according to reaction conditions which are well known to a person skilled in the art.

The present invention also relates to the use of the oligomers described above.

These oligomers can be used to produce polymers having flame-retardant properties. To this end, the present invention also relates to the polymerisation of an oligomer as defined above. This is because, in view of the existence of free acrylate functional groups in the oligomer, the latter lends itself well to polymerisation under irradiation, under ultraviolet or infrared or by electron bombardment, or by heat in the presence or absence of thermal initiators based on peroxides or initiators of azo type (azobisisobutyronitrile). The polymerisation of the oligomer preferably takes place under irradiation, under ultraviolet or by electron bombardment. Good results have been obtained with polymerisation under irradiation.

The present invention also relates to a composition which can be cross-linked by irradiation and which has flame-retardant properties. The composition comprises at least one oligomer as defined above. The composition optionally comprises one or more monomers which can be cross-linked by irradiation and optionally a photoinitiator.

The term "monomer" is understood to mean a compound which does not comprise halogen and which can be polymerised by irradiation. Usually, an organic monomer comprising an acrylic or vinyl functional group is employed. Mention may be made, as examples of appropriate monomers, of diethylene glycol diacrylate, tripropylene glycol diacrylate, hexanediol diacrylate, tetrahydrofurfuryl acrylate, methoxyethyl acrylate, ethoxyethoxyethyl acrylate, trimethyloylpropane triacrylate or pentaerythritol triacrylate (PETIA).

The composition usually comprises from 0 to 60% by weight of monomers which can be cross-linked by irradiation, preferably from 25 to 45%. The content of the latter is adjusted according to the use of the composition and according to the viscosity desired for the application of the composition.

If the composition has to be polymerised by ultraviolet radiation, a photoinitiator is preferably added. Numerous photoinitiators are already known. Appropriate photoinitiators are in particular 1-hydroxycyclohexyl phenyl ketone or a mixture of 2-hydroxy-2-methyl-1-phenylpropan-1-one and 2,4,6-trimethylbenzoyldiphenylphosphine oxide.

The composition can also comprise other additives, such as stabilisers, plasticisers, adhesion promoters, chain-transfer agents or compounds comprising unsaturations which can be cross-linked by irradiation in order to adjust the viscosity.

The composition of the invention is preferably devoid of halogen.

The present invention also relates to the use of the composition described above.

The composition of the invention is applied to any substrate, such as textile, textile fibre, such as cellulose fibres, wood, optical fibre, metal, such as iron, copper, aluminium or steel, glass, paper and plastics, such as polyethylene and polypropylene.

It is employed as flame-retardant coating or covering.

The composition of the invention can also be added to paints and adhesives.

The term "flame-retardant composition" is understood to mean a sample which exhibits an LOI (LOI: Limiting Oxygen Index) of greater than 20% when subjected to the oxygen index text described in the American Standard Testing Method (ASTM) D 2863. A material possessing an LOI index of greater than 20% is regarded as slow burning (LOI index between 20% and 26%) or self-extinguishing (LOI>27%) according to the publication by M. Levin, S. M. Atlas and Eli M. Pearce, "Flame-Retardant Polymeric Materials", Published by Plenum Press, New York (1975), page 376. All the oligomers of the invention exhibit an LOI of greater than 20% and therefore correspond to the definition of materials possessing flame-retardant properties.

In view of their adhesion to highly varied substrates, the polymerised compositions can have a great many industrial applications, such as thin, thick or semi-thick coatings on all the above mentioned substrates. Furthermore, the composition comprising a phosphorus-comprising polyol which is the reaction product of a phosphonic acid and which carries unreacted acid groups exhibits good properties of adhesion to metal substrates.

The phosphorus-comprising polyols and the oligomers according to the invention are virtually colourless. Their colour, measured according to the Gardner method, is less than or equal to 3 G and generally less than or equal to 2 G. This has the advantage of having virtually no influence on the colour of the substrate or of the composition.

The present invention will now be illustrated by the following, non-limiting Examples.

In the Examples the following conventional techniques were used well known to those skilled in the art: acid numbers were measured using ASTM D 974-64; epoxy values were measured using ASTM E 200; hydroxy (OH) numbers were measured using ASTM E 222-73; NCO numbers were measured using ASTM D 2572-87; Hoppler viscosity (H) was measured at 25° C. using DIN 53015; and colour was measured using the Gardner method as described in ASTM 1544-68.

Standard Preparation of Urethane-acrylates Used in Some Examples

Examples 2, 4, 6, 8, 10, 12, 14, 16 and 18 herein used the following standard method to prepare a phosphorus-comprising urethane-acrylate from exemplified phosphorus comprising polyols. Amounts "a" g of isophorone diisocyanate (IPDI), "b" mg of di-tert-butylhydroquinone (DtBHQ), "c" mg of trinonylphenyl phosphite (TNPP) and "d" mg of triphenylstibine (TFS) were introduced into a 2 litre jacketed reactor vessel connected to a thermostatically-controlled oil bath and equipped with a stirrer. The reaction mixture was heated to 40° C. at atmospheric pressure and "e" mg of dibutyl tin dilaurate (DBTL) was added to the vessel at this temperature. Then "f" g of a phosphorus-comprising polyol (that prepared as described in Example "g") were added to the vessel via a gauge over a period of one hour whilst the temperature was held at approximately 60° C. When the NCO number was less than "h" meq/g, a mixture of "i" g of hydroxyethyl acrylate (HEA), "i" g of hexanediol diacrylate (HDDA) and "k" mg of DBTL was added to the vessel via a gauge over a period of one hour whilst the temperature was kept between 60 and 70° C. After this was done, "l" mg of TFS and "m" mg of DtBHQ were added and the mixture was heated at 90° C. until the NCO number was less than 0.15% (0.036 meq/g). The product obtained was a phosphorus comprising urethane-acrylate. Values for "a" to "m" for each of these Examples are given in Table 1.

following properties: H=3000 mP·s; and Gardner colour<3 G. This urethane-acrylate was applied to various substrates using a film drawer. The properties of the films formed were tested.

A film with a thickness of 150 μm was obtained by electron bombardment [electron beam (EB) curing (reactivity: 2 Mrad, 250 keV; substrate: stainless steel plate)]. The film exhibited the following properties: the

TABLE 1

(standard preparation of urethane-acrylates)

| Ex | "a" (IPDI/ g) | "b" (DtHQ/ mg) | "c" (TNPP/ mg) | "d" (TFS/ mg) | "e" (DBTL/ mg) | "f" (polyol/ g) | "g" (polyol/ Ex) | "h" (NCO/ meq g$^{-1}$) | "i" (HEA/ g) | "j" (HDDA/ g) | "k" (DBTL/ mg) | "l" (TFS/ mg) | "m" (DtHQ/ mg) |
|---|---|---|---|---|---|---|---|---|---|---|---|---|---|
| 2 | 87 | 166 | 166 | 332 | 100 | 200 | 1 | 2.88 | 45 | 100 | 100 | 332 | 166 |
| 4 | 135 | 300 | 300 | 600 | 100 | 233 | 3 | 1.66 | 70 | 110 | 100 | 600 | 300 |
| 6 | 177 | 300 | 300 | 600 | 100 | 250 | 5 | 1.87 | 93 | 155 | 100 | 600 | 300 |
| 8 | 222 | 500 | 500 | 1000 | 150 | 485 | 7 | 1.45 | 116 | 245 | 150 | 1000 | 500 |
| 10 | 222 | 500 | 500 | 1000 | 150 | 524 | 9 | 1.35 | 116 | 192 | 100 | 1000 | 500 |
| 12 | 83 | 250 | 250 | 500 | 70 | 263 | 11 | 1.10 | 44 | 98 | 70 | 500 | 250 |
| 14 | 55 | 250 | 250 | 500 | 70 | 300 | 13 | 0.70 | 29 | 128 | 70 | 500 | 250 |
| 16 | 166 | 500 | 500 | 1000 | 150 | 302 | 15 | 1.60 | 87 | 139 | 150 | 1000 | 500 |
| 18 | 222 | 500 | 500 | 1000 | 150 | 339 | 17 | 1.8 | 120 | 225 | 150 | 1000 | 150 |

EXAMPLE 1

A phosphorus-comprising polyol was prepared as follows. An amount of 420 g (1.31 eq) of a polypropylene glycol diepoxide available commercially from Dow under the trade designation DER 732 (with an epoxy value of 320 g/eq), was introduced into a 2 litre jacketed reactor vessel connected to a thermostatically-controlled oil bath and equipped with a stirrer. The diepoxide was heated to 70° C. at atmospheric pressure. Then 276 g (1.31 eq) of dibutyl phosphate was introduced into the vessel via a gauge over a period of one hour while the reaction mixture was stirred and the temperature was kept at 70° C. After the dibutyl phosphate had been completely added, the mixture was heated at 90° C. for 3 hours. An additional amount of the diepoxide used previously (DER 732 in this case) was then added in small portions, to bring the acid number below 10 mg KOH/g and the epoxy value below 0.5% (0.12 meq/g). The product obtained was a phosphorus-comprising polyol with the following properties: OH number=110 mg KOH/g, acid number=2.7 mg KOH/g, epoxy value=0.11 meq/g, H=637 mPa·s; and Gardner colour<1 G.

EXAMPLE 2

A urethane-acrylate was prepared by the standard method described herein with reference to Table 1 and exhibited the following properties: H=2,458 mPa·s; and Gardner colour<1 G.

EXAMPLE 3

A polyol was prepared analogously to the method described in Example 1, where 180 g (0.86 eq) of the dibutyl phosphate was used and the initial amount of diepoxide was 163 g (0.86 eq) of a polypropylene glycol diepoxide available commercially from Dow under the trade designation DER 736 (with an epoxy value of 190 g/eq). The product obtained was a phosphorus-comprising polyol with the following properties: OH number=147 mg KOHtg; acid number=6.44 mg KOH/g; epoxy value=0.5% (0.12 meq/g); H=1,680 mP·s; and Gardner colour<1 G.

EXAMPLE 4

A urethane-acrylate was prepared by the standard method described herein with reference to Table 1 and exhibited the number of double rubs of the film with acetone required to expose a paper substrate (acetone double rubs) was greater than 100; on a glass substrate the Persoz hardness (oscillations) was in the region of 43; and the LOI number was 23.0 to 23.3%, measured according to ASTM D 2863-91.

A film with a thickness of 100 μm was obtained by ultraviolet (UV) curing (medium pressure mercury lamp; 80 Watt/cm) in the presence of 4% of a photoinitiator (that available commercially from Ciba under the trade name Irgacure 500). The film exhibited the following properties: on a paper substrate reactivity was 10 metres/min (cure speed) and 5 metres/min (talc speed); acetone double rubs>100; and on a glass substrate the Persoz hardness (oscillations) was in the region of 97.

EXAMPLE 5

A polyol was prepared analogously to the method described in Example 1, where 230 g (1.10 eq) of the dibutyl phosphate was used and the initial amount of diepoxide was replaced by 140 g (1.10 eq) of a 1,4-butanediol diglycidyl ether available commercially from Shell under the trade name Heloxy 67 (with an epoxy value of 127 g/eq). The product obtained was a phosphorus-comprising polyol with the following properties: OH number=179 mg KOH/g; acid number=5.7 mg KOH/g; epoxy value<0.01 meq/g, Hoppler viscosity=2,020 mP·s; and Gardner colour<1 G.

EXAMPLE 6

A urethane-acrylate was prepared by the standard method described herein with reference to Table 1 and exhibited the following properties: H=6,600 mP·s; and Gardner colour<3 G.

EXAMPLE 7

A polyol was prepared analogously to the method described in Example 1, where 758 g (3.61 eq) of the dibutyl phosphate was used and the initial amount of diepoxide was 460 g (3.61 eq) of a cycloaliphatic diepoxide manufactured by Daicel and available commercially from UCB S.A. under the trade names Uvacure 1500 or Celloxide 2021 P (with an epoxy value of 127 g/eq). Also after the dibutyl phosphate was added as described in Example 1, the temperature of the reaction mixture was raised to 90° C. and held there until the acid number was below 5 mg KOH/g and the epoxy value was below 0.5% (0.12 meq/g). The product obtained was a phosphorus-comprising polyol with the following properties: OH number=116 mg KOH/g; acid number=10 mg KOH/g; epoxy value<0.05 meq/g; H=17,750 mP·s; and Gardner colour<1 G.

EXAMPLE 8

A urethane-acrylate was prepared by the standard method described herein with reference to Table 1 and exhibited the following properties: H=11,800 mP·s; and Gardner colour<1 G. This urethane-acrylate was applied to various substrates using a film drawer and the properties of the films formed were tested as described below.

A 150 μm film prepared and tested analogously to the methods described in Example 4, exhibited the following properties: acetone double rubs>100; and Persoz hardness in the region of 97.

A 100 μm film prepared and tested analogously to the methods described in Example 4, exhibited the following properties: on a paper substrate reactivity was 5 metres/min (cure speed) and 5 metres/min (talc speed); acetone double rubs>100; and Persoz hardness (oscillations) was in the region of 63.

EXAMPLE 9

A polyol was prepared analogously to the method described in Example 1, where 420 g (2 eq) of the dibutyl phosphate was used and the initial amount of diepoxide was 366 g (2 eq) of a cycloaliphatic diepoxide available commercially from Daicel under the trade name Celloxide 2081 (with an epoxy value of 183 g/eq). The product obtained was a phosphorus-comprising polyol with the following properties: OH number=107 mg KOH/g, acid number=4.6 mg KOH/g, epoxy value<0.02 meq/g, H 8,500 mP·s; and Gardner colour<1 G.

EXAMPLE 10

A urethane-acrylate was prepared by the standard method described herein with reference to Table 1 and exhibited the following properties: H=13,200 mP·s; and Gardner colour<1 G.

EXAMPLE 11

A polyol was prepared analogously to the method described in Example 1, where 420 g of the dibutyl phosphate was used and the initial amount of diepoxide was 609 g of a cycloaliphatic diepoxide available commercially from Daicel under the trade name Celloxide 2083 (with an epoxy value of 297 g/eq). The product obtained was a phosphorus-comprising polyol with the following properties: OH number=80 mg KOH/g, acid number=1.98 mg KOH/g, epoxy value<0.02 meq/g, H=12,800 mPa·s; and Gardner colour<1 G.

EXAMPLE 12

A urethane-acrylate was prepared by the standard method described herein with reference to Table 1 and exhibited the following properties: H=4,800 mP·s; and Gardner colour<1 G.

EXAMPLE 13

A polyol was prepared analogously to the method described in Example 1, where 79 g (0.38 eq) of the dibutyl phosphate was used and the initial amount of diepoxide was 156 g of a cycloaliphatic diepoxide available commercially from Daicel under the trade name Celloxide 2085 (with an epoxy value of 411 g/eq). The product obtained was a phosphorus-comprising polyol, solid at room temperature, with the following properties: OH number=67 mg KOH/g, acid number=2.2 mg KOH/g, epoxy value<0.05 meq/g; and Gardner colour<1 G.

EXAMPLE 14

A urethane-acrylate was prepared by the standard method described herein with reference to Table 1 and exhibited the following properties: H=1,400 mPa·s; and Gardner colour<1 G.

EXAMPLE 15

A polyol was prepared analogously to the method described in Example 1, where 430 g (2.05 eq) of the dibutyl phosphate was used and the diepoxide was replaced by a dioxetane initially in an amount of 342 g (2.05 eq) of a dioxetane 1,4-bis[(3ethyl-3-oxetanylmethoxy)methyl] benzene available commercially from Toagosei under the trade designation XDO (with an epoxy value of 167 g/eq). The product obtained was a phosphorus-comprising polyol with the following properties: OH number=139 mg KOH/g, acid number=11.1 mg KOH/g, oxetane value (measured analogously to the epoxy value)<0.10 meq/g; H=2,400 mP·s; and Gardner colour<1 G.

EXAMPLE 16

A urethane-acrylate was prepared by the standard method described herein with reference to Table 1 and exhibited the following properties: H=13,900 mP·s; and Gardner colour<1 G.

EXAMPLE 17

A polyol was prepared analogously to the method described in Example 1, where 420 g (2.0 eq) of the dibutyl phosphate was used and the initial amount of diepoxide 425 g (2.0 eq) of an aromatic diepoxide [a bisphenol A diglycidyl ether available commercially from Dow under the trade name Epikote 828 (with an epoxy value of 200 g/eq)]. The product obtained was a phosphorus-comprising polyol with the following properties: OH number=166 mg KOH/g, acid number=8.0 mg KOH/g, epoxy value<0.10 meq/g; H=230,000 mP·s; and Gardner colour<1 G.

EXAMPLE 18

A urethane-acrylate was prepared by the standard method described herein with reference to Table 1 and exhibited the following properties: H=3,100 mP·s; and Gardner colour<1 G.

EXAMPLE 19

A phosphorus-comprising polyol was prepared as follows. Amounts of 262 g (1.5 eq) of a cresol novolak available commercially from Dow Chemical under the trade designation DEN 431 (with epoxy value of 175 g/eq) and 316 g of hexanediol diacrylate (HDDA) were introduced into a 2 litre jacketed reactor connected to a thermostatically-controlled oil bath and equipped with a stirrer. The reaction mixture was heated to 100° C. at atmospheric pressure. To the stirred contents of the vessel was added a mixture of 158 g (0.75 eq) of dibutyl phosphate, 54 g (0.75 eq) of acrylic acid, 1.2 g of AMC-2 as catalyst and 600 mg of hydroquinone via a gauge over a period of one hour whilst the temperature of the reaction mixture was kept below 110° C. Air was injected into the vessel throughout the reaction. At the end of the addition, the reaction mixture was kept at 110° C. for 3 hours. Additional cresol novolak was subsequently added in portions, to bring the acid number to a value of less than 10 mg KOH/g and the epoxy value to less than 0.5% (0.12 meq/g). The product obtained was a phosphorus-comprising polyol with the following properties: OH number=130 mg KOH/g, acid number=4.5 mg KOH/g, epoxy value=0.10 meq/g; H=1,375 mP·s; and Gardner colour<1 G.

EXAMPLE 20

A phosphorus-comprising polyol was prepared as follows. Amounts of 285 g (1.5 eq) of the DER 736 diepoxide (described in Example 3), and 237 g (1.5 mol, 3 eq) of phenylphosphonic acid were introduced into a 2 litre jacketed reactor connected to a thermostatically-controlled oil bath and equipped with a stirrer. The mixture was slowly heated until an exotherm was observed, following which the mixture was brought to 90° C. until the acid number was below 162 mg KOH/g and the epoxy value was below 0.5% (0.12 meq/g). The mixture was then diluted with 440 g of HDDA. The product obtained was a phosphorus-comprising polyol, solid at room temperature, with the following properties: acid number=158 mg KOH/g; epoxy value<0.01 meq/g; and Gardner colour<3 G. The OH number of the product could not be measured by the usual method because of the presence of acid groups, but was estimated by calculation to be 161 mg KOH/g.

EXAMPLE 21

A polyol was prepared analogously to the method described in Example 20, where the phosphonic acid was replaced by 213 g (1.5 mol; 1.5 eq) of phenylphosphinic acid and the additional diepoxide was added to bring the acid number below 10 mg KOH/g and the epoxy value below 0.5% (0.12 meq/g). The product obtained was a phosphorus-comprising polyol, very viscous at room temperature, with the following properties: epoxy value<0.01 meq/g; and Gardner colour<1 G. The OH and acid numbers of the product could not be measured by the usual methods because of the presence of acid groups. Nevertheless these values can be estimated by calculation.

What is claimed is:

1. Phosphorus-comprising polyol comprising at least two terminal phosphate esters or at least two terminal phosphonate esters or at least one terminal phosphate ester and one terminal phosphonate ester, and said polyol being the reaction product of at least one polyoxirane and of at least one phosphorus-comprising compound selected from phosphoric acid esters, phosphonic acid esters, phosphonic acids and phosphinic acids.

2. Phosphorus-comprising polyol according to claim 1, wherein the polyoxirane is chosen from polypropylene glycol diepoxides, 1,4-butanediol glycidyl ether, the diepoxides of the formula (X) or (XI), 1,4-bis[(3-ethyl-3-oxetanylmethoxy)methyl]benzene, bisphenol A diglycidyl ether and the cycloaliphatic polyepoxides of general formula (VI), and wherein the phosphorus-comprising compound is chosen from dibutyl phosphate, phenylphosphonic acid and phenylphosphinic acid.

3. Phosphorus-comprising polyol according to claim 1, corresponding to the general formula (XIV):

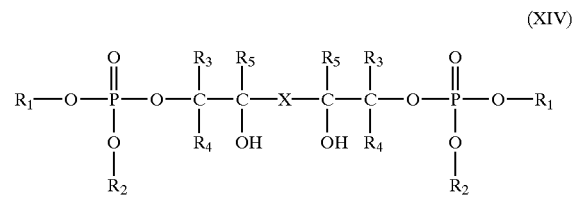

(XIV)

in which

X represents a substituted or unsubstituted, divalent, linear or branched alkyl, cycloaliphatic or aromatic radical having from 1 to 50 carbon atoms which can optionally comprise oxygen atoms; or X represents a divalent group of general formula

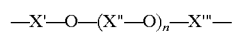

in which n represents an integer from 1 to 50 and X', X" and X''' independently represent a substituted or unsubstituted, divalent, linear or branched alkyl, cycloaliphatic or aromatic radical having from 1 to 80 carbon atoms;

$R_1$, $R_2$, $R_2'$ and $R_2'$ independently represent a substituted or unsubstituted, aliphatic, cycloaliphatic or aromatic radical having from 1 to 16 carbon atoms;

$R_3$, $R_4$, $R_3'$ and $R_4'$ independently represent a hydrogen atom or a substituted or unsubstituted, linear or branched alkyl, cycloaliphatic or aromatic radical having from 1 to 25 carbon atoms; and $R_5$ and $R_5'$ independently represent a hydrogen atom or a substituted or unsubstituted, linear or branched alkyl, cycloaliphatic or aromatic radical having from 1 to 25 carbon atoms.

4. Phosphorus-comprising polyol according to claims 1, characterized in that it corresponds to the general formula (XV):

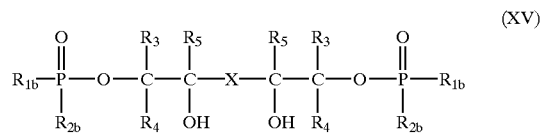

(XV)

in which

X represents a substituted or unsubstituted, divalent, linear or branched alkyl, cycloaliphatic or aromatic radical having from 1 to 50 carbon atoms which can optionally comprise oxygen atoms; or X represents a divalent group of general formula

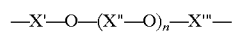

in which n represents an integer from 1 to 50 and X', X" and X''' independently represent a substituted or unsubstituted, divalent, linear or branched alkyl, cycloaliphatic or aromatic radical having from 1 to 80 carbon atoms;

$R_{1b}$ and $R_{1b}'$ represent a hydroxyl radical, substituted or unsubstituted oxyalkyl or oxyaryl radical comprising from 1 to 16 carbon atoms or a hydrogen atom; and $R_{2b}$ and $R_{2b}'$ represent a substituted or unsubstituted, aliphatic, cycloaliphatic or aromatic radical having from 1 to 16 carbon;

$R_3$, $R_4$, $R_3'$ and $R_4'$ independently represent a hydrogen atom or a substituted or unsubstituted, linear or branched alkyl, cycloaliphatic or aromatic radical having from 1 to 25 carbon atoms; and $R_5$ and $R_5'$ independently represent a hydrogen atom or a substituted or unsubstituted, linear or branched alkyl, cycloaliphatic or aromatic radical having from 1 to 25 carbon atoms.

5. Process for the preparation of the phosphorus-comprising polyol according to claim 1, which comprises the reaction of at least one polyoxirane and of at least one phosphorus-comprising compound chosen from phosphoric acid esters, phosphonic acid esters, phosphonic acids and phosphinic acids.

6. Process according to claim 5, wherein at least one equivalent of oxirane radical carried by the polyoxirane is employed per mol of phosphorus-comprising compound.

7. Oligomer, which is the product of the reaction of a phosphorus-comprising polyol according to claim 1, of a polyisocyanate and of a hydroxylated acrylate.

8. Oligomer, which is the product of the reaction of a phosphorus-comprising polyol according to claim 1 and of alkylesters of acrylic acid or of methacrylic acid.

9. Polymer, which is obtained by polymerization of an oligomer according to claim 7 under irradiation.

10. Composition comprising an oligomer according to claim 7 and a monomer which can be cross-linked by irradiation.

11. Polymer, which is obtained by polymerization of an oligomer according to claim 8 under irradiation.

12. Composition comprising an oligomer according to claim 8 and a monomer which can be cross-linked by irradiation.

13. Composition comprising a polymer according to claim 9 and a monomer which can be cross-linked by irradiation.

14. Phosphorus-comprising polyol according to claim 2 wherein the cycloaliphatic polyepoxide of general formula (VI) is cresol novolak.

\* \* \* \* \*